US006387382B1

United States Patent
Saleh et al.

(10) Patent No.: US 6,387,382 B1
(45) Date of Patent: May 14, 2002

(54) WATER-PROOF, RESPIRABLE, SKIN BARRIER COMPOSITION

(75) Inventors: Michael Saleh, Hacienda Heights; Kimberly A Leahy, Trabuco Canyon, both of CA (US)

(73) Assignee: Axiom Laboratories, Inc., Huntington Beach, CA (US)

( * ) Notice: Subject to any disclaimer, the term of this patent is extended or adjusted under 35 U.S.C. 154(b) by 0 days.

(21) Appl. No.: 09/197,999

(22) Filed: Nov. 23, 1998

(51) Int. Cl.$^7$ .................. A61K 31/695; A61K 9/10
(52) U.S. Cl. .................. 424/401; 424/725; 424/747; 424/729; 424/764; 514/63; 514/844; 514/938
(58) Field of Search .................. 424/401, 725, 424/747, 729, 764; 514/844, 938, 63

(56) References Cited

U.S. PATENT DOCUMENTS

| | | | |
|---|---|---|---|
| 3,541,205 A | 11/1970 | Hardigan et al. | 424/60 |
| 4,370,319 A | 1/1983 | Chapin et al. | 424/184 |
| 4,421,769 A | 12/1983 | Dixon et al. | 424/358 |
| 4,563,346 A | 1/1986 | Deckner | 424/59 |
| 4,782,095 A | 11/1988 | Gum | 514/937 |
| 4,784,844 A | 11/1988 | Thimineur et al. | 424/65 |
| 4,801,447 A | 1/1989 | Gum | 424/68 |
| 4,822,602 A | 4/1989 | Sabatelli | 424/65 |
| 4,847,071 A | 7/1989 | Bissett et al. | 424/59 |
| 4,847,267 A | 7/1989 | Deckner et al. | 514/311 |
| 4,917,891 A | 4/1990 | Kaufmann et al. | 424/401 |
| 4,960,764 A | 10/1990 | Figueroa, Jr. et al. | 514/63 |
| 4,963,591 A | 10/1990 | Fourman et al. | 514/944 |
| 4,980,167 A | 12/1990 | Harishima et al. | 424/401 |
| 5,013,763 A | 5/1991 | Tubesing et al. | 514/772 |
| 5,036,108 A | 7/1991 | Asahi et al. | 514/937 |
| 5,041,281 A | 8/1991 | Strobridge | 424/59 |
| 5,066,485 A | 11/1991 | Brieva et al. | 424/63 |
| 5,103,812 A | 4/1992 | Salamone et al. | 602/52 |
| 5,106,609 A | 4/1992 | Bolich, Jr. et al. | 424/70 |
| 5,118,507 A | 6/1992 | Clement | 424/401 |
| 5,143,722 A | 9/1992 | Hollenberg et al. | 424/63 |
| 5,162,378 A | 11/1992 | Guthauser | 514/785 |
| 5,208,013 A | 5/1993 | Klein | 424/59 |
| 5,216,033 A | 6/1993 | Pereira et al. | 514/844 |
| 5,234,689 A | 8/1993 | Lindauer et al. | 424/401 |
| 5,292,503 A | 3/1994 | Raleigh et al. | 424/59 |
| 5,292,529 A | 3/1994 | Gregory et al. | 424/70 |
| 5,302,382 A | 4/1994 | Kasprzak | 424/78.03 |
| 5,362,482 A | 11/1994 | Yoneyama et al. | 424/69 |
| 5,380,528 A | 1/1995 | Alban et al. | 424/401 |
| 5,384,115 A | 1/1995 | Bissett et al. | 424/59 |
| 5,387,417 A | 2/1995 | Rentsch | 424/401 |
| 5,389,363 A | 2/1995 | Snyder et al. | 424/70.7 |
| 5,397,566 A | 3/1995 | Thimineur et al. | 424/70.12 |
| 5,407,958 A | 4/1995 | Heath et al. | 424/28.06 |
| 5,411,729 A | 5/1995 | O'Lenick, Jr. | 424/70.12 |
| 5,413,781 A | 5/1995 | Giwa-Agbomeirele et al. | 424/78.03 |
| 5,420,118 A | 5/1995 | Alban et al. | 514/63 |
| 5,435,996 A | 7/1995 | Glover et al. | 424/78.03 |
| 5,443,760 A | 8/1995 | Kasprzak | 424/78.03 |
| 5,451,610 A * | 9/1995 | Krzysik | |
| 5,472,686 A | 12/1995 | Tsubaki et al. | 424/59 |
| 5,482,714 A | 1/1996 | Jones et al. | 424/401 |
| 5,523,081 A | 6/1996 | Edwards et al. | 424/73 |
| 5,525,344 A | 6/1996 | Wivell | 424/401 |
| 5,531,986 A | 7/1996 | Shevade et al. | 424/68 |
| 5,549,887 A | 8/1996 | Galleguillos et al. | 424/66 |
| 5,552,135 A | 9/1996 | Cioca et al. | 424/59 |
| 5,567,426 A | 10/1996 | Nadaud et al. | 424/401 |
| 5,578,641 A | 11/1996 | Jackson et al. | 514/547 |
| 5,589,165 A | 12/1996 | Yoshida et al. | 424/78.03 |
| 5,599,533 A | 2/1997 | Stepniewski et al. | 424/78.02 |
| 5,599,800 A | 2/1997 | Candau | 514/53 |
| 5,626,857 A | 5/1997 | Thimineur et al. | 424/401 |
| 5,648,083 A | 7/1997 | Bliezner et al. | 424/402 |
| 5,650,159 A | 7/1997 | Lion et al. | 424/401 |
| 5,658,559 A | 8/1997 | Smith | 424/78.02 |
| 5,674,508 A | 10/1997 | Deserable et al. | 487/848 |
| 5,695,772 A | 12/1997 | Kanga et al. | 424/401 |
| 5,725,845 A | 3/1998 | Krog et al. | 424/64 |
| 5,776,494 A | 7/1998 | Guskey et al. | 424/484 |
| 5,798,111 A | 8/1998 | Kanga et al. | 424/401 |
| 5,800,816 A | 9/1998 | Brieva et al. | 424/63 |
| 5,804,205 A | 9/1998 | Epstein et al. | 424/401 |
| 6,001,374 A * | 12/1999 | Nichols | |

OTHER PUBLICATIONS

International Cosmetic Ingredient Dictionary and Handbook, Cosmetic, Toiletry, and Fragrance Association, Wash. D.C., 7$^{th}$ Ed., (1997).

Rose et al. Burns, vol. 23, Supplement 1, pp. S19–S26 (1997). Date missing.

* cited by examiner

*Primary Examiner*—Raj Bawa
(74) *Attorney, Agent, or Firm*—Lawrence J. McCuse; Karin E. Paterka; Norton R. Townsley

(57) ABSTRACT

Multipurpose skin preparations in the form of oil-in-water emulsions are disclosed. The skin preparations are prepared by combining an oil phase and an aqueous phase. The oil phase comprises a siloxane polymer, a cyclic silicone, an anti-oxidant, and an emollient. In a second version of the present invention, the oil phase includes a copolymer comprising PPG-12/SMDI. The aqueous phase comprises at least a humectant, a rheology modifier, a thickener, and water. The inventive preparations are useful in topical application to the skin, are highly water resistant, remain on the skin after multiple washings, form a protective barrier on the skin, and effectively deliver and maintain moisturizing and therapeutic agents on the skin. It is believed that the skin preparations of the present invention also effectively deliver and maintain moisturizing and select therapeutic agents, biological agents, pharmaceutical agents, and the like, which are useful for the treatment of pathologies of the skin.

11 Claims, No Drawings

WATER-PROOF, RESPIRABLE, SKIN BARRIER COMPOSITION

BACKGROUND

The present invention relates to multipurpose skin preparations in the form of oil-in-water emulsions. More particularly, the present invention relates to oil-in-water emulsions containing a combination of silicones. Such oil-in-water emulsions, when blended in accordance with the teaching of the present invention, provide excellent water-proof, cross-linked, respirable, and protective barriers on the skin, provide superior tactile properties, and effectively deliver and maintain moisturizing and therapeutic agents on the skin. It is believed that the skin preparations of the present invention also effectively deliver and maintain moisturizing and therapeutic agents useful for the treatment of pathologies of the skin.

The skin has a naturally produced sebum layer which acts as a barrier to protect the skin from external factors and prevent the escape of moisture from the skin. This natural sebum layer barrier dissipates with age. Low humidity, harsh soaps and chemicals, and excessive bathing and washing further accelerate the removal of the sebum layer from the skin. With the loss of this barrier, the skin loses its ability to retain water, is left unprotected from external factors, and, consequently, pathologies of the skin often result.

It is known that certain professions require constant washing of the hands and/or constant exposure of the skin to detergents, harsh chemicals, and water-borne irritants. For instance, physicians are required to thoroughly wash their hands both prior to and after seeing a patient or performing a surgical procedure. Therefore, physicians may wash their hands repeatedly throughout the day. These repeated washings may dry, damage and otherwise harm the skin. Furthermore, the hands of hair stylists and beauty salon employees may be continually exposed to detergents, chemicals, and water-borne irritants when performing hair care, nail care, and other personal care services for clients. These repeated exposures to such irritants may likewise dry, damage and otherwise harm the skin.

Such professionals, as well as people in the medical industry, cosmetic industry, consumers, and people with skin disorders, typically use known oil-in-water emulsions, such as lotions and creams, to alleviate dryness and chapping that may be caused by repeated washings of the skin. In general, such oil-in-water emulsions contain water and known ingredients such as emollients, emulsifiers, antioxidants, skin conditioners, preservatives, humectants, thickeners, cleansers, colorants, fragrances, and other ingredients generally used in the cosmetic art. However, many such known preparations lack good tactile properties and may create a sticky, oily, greasy, or waxy feel when applied to the skin. In addition, many such known preparations do not stay on the skin after a single washing with soap and water and must be reapplied after each washing. This decreases the effectiveness of the preparations and increases the costs to businesses such as hospitals and salons which require a constant supply of such lotions and creams for use by employees. In addition, many such known preparations contain undesirable ingredients such as perfumes and colorants which may cause allergic reactions when applied to the skin.

Moreover, the use of silicones in oil-in-water emulsions is also known. Silicones are found in a number of personal care products and are especially desirable for their water repellency, superior emolliency and lubricity, and for facilitating the formation of thin coatings on the skin that do not impart a greasy or sticky feeling. However, such known skin preparations or compositions containing silicones may require use of a large amount of silicones, i.e., greater than 20% by weight of the total composition, in order to sufficiently impart the beneficial properties of such silicones. Because silicones are generally expensive, use of such large amounts of silicones in skin preparations can increase manufacturing costs. In addition, since silicones have limited solubility in water, use of large amounts of silicones can limit the ability to form effective oil-in-water emulsions. Moreover, applicants are unaware of any known skin preparations containing silicones that stay on the skin and provide a protective barrier for up to 3 to 6, or more, washings of the skin surface, where each washing is made with soap and water for an average of 15–20 seconds long.

Thus, a need exists for skin preparations that provide superior tactile properties; that impart a silky, smooth and non-greasy feel when applied to the skin; that provide water-proof, cross-linked, respirable barriers on the skin; that protect the skin from water-borne irritants, deleterious chemicals, and other external factors; that provide resistance to repeated exposures to water and detergents; that prevent moisture from escaping from the skin and seal in moisture for up to hours; that act like the skin's naturally produced protective barrier (sebum layer), while also acting as a medium for the introduction of therapeutic agents to the skin, such that the efficacy of these therapeutic agents is amplified by the barrier function of the skin preparations since the therapeutic agents remain on the skin for long periods of time; that facilitate the healing of damaged skin as a result of cuts, scratches, burns, and other abuses of the skin; that substantially remain on the skin after multiple washings, that is, that maintain and provide a protective barrier on the skin for up to 3 to 6, or more, washings of the skin surface, where each washing is made with soap and water for an average of 15–20 seconds long; that contain sufficiently low, less costly amounts of silicones yet maintain all of the beneficial properties of known preparations containing higher, more costly amounts of silicones; that it is believed when combined with select therapeutic agents, biological agents, pharmaceutical agents, and/or steroids, facilitate the healing of a variety of skin pathologies; that form oil-in-water emulsions having good viscosity, stability, and proccessability; and that are easy and cost efficient to manufacture.

Although attempts have been made to produce such skin preparations, to date, applicants are unaware of such multipurpose skin preparations that provide all of the advantages of the present invention. For the foregoing reasons, there is a need for multipurpose skin preparations that provide all of these advantages.

SUMMARY

The present invention is directed to multipurpose skin preparations that satisfy these needs. A first version of a skin preparation having features of the present invention is prepared by combining an oil phase and an aqueous phase. The oil phase is prepared by combining by total weight of the skin preparation the following: (i) at least 2% by weight of a siloxane polymer; (ii) at least 1% by weight of a cyclic silicone, and wherein the siloxane polymer and cyclic silicone are present in a respective weight ratio in the range of from about 2:1 to about 7:1; (iii) at least 1.5% by weight of at least one emulsifier; (iv) at least 0.1% by weight of at least one antioxidant; and, (v) at least 2% by weight of at least one emollient. The aqueous phase is prepared by combining by total weight of the skin preparation the following: (i) at least 0.1% by weight of at least one humectant; (ii) at least 0.1% by weight of at least one rheology modifier; (iii) at least 0.1% by weight of at least one thickener; and, (iv) water. The silxoane polymer may comprise dimethicone, trimethylsiloxysilicate, or mixtures thereof The siloxane polymer and cyclic silicone are preferably in sufficient amounts such that after the skin preparation is applied to the skin and a cross-linked protective coating is formed on the skin, when the skin is washed up to 3 to 4 times with soap and water for an average of 15–20 seconds each wash, the skin preparation maintains a protective barrier on the skin, wherein a protective barrier is one that is water-proof and prevents moisture from escaping from the skin and wherein at least about 75% of the skin preparation originally applied to the skin remains on the skin after each washing.

A second version of a skin preparation having features of the present invention is also prepared by combining an oil phase and an aqueous phase. The oil phase is prepared by combining by total weight of the skin preparation the following: (i) at least 2% by weight of a siloxane polymer; (ii) at least 1% by weight of a cyclic silicone; (iii) at least 0.8% by weight of a copolymer formed from an isocyanate monomer and a polyol; (iv) at least 1.5% by weight of at least one emulsifier; (v) at least 0.1% by weight of at least one antioxidant; and, (vi) at least 2% by weight of at least one emollient. The aqueous phase is prepared by combining by total weight of the skin preparation the following: (i) at least 0.1% by weight of at least one humectant; (ii) at least 0.1% by weight of at least one rheology modifier; (iii) at least 0.1% by weight of at least one thickener; and, (iv) water. The siloxane polymer and cyclic silicone of this version may be present in a respective weight ratio in the range of from about 2:1 to about 7:1. The siloxane polymer may comprise dimethicone, trimethylsiloxysilicate, phenyl trimethicone, or mixtures thereof. The copolymer may comprise polyolprepolymer-2 (PPG-12/SMDI copolymer) in a sufficient amount such that when combined with the other silicones, after the skin preparation is applied to the skin and a protective cross-linked, respirable coating is formed on the skin, when the skin is washed up to 5 to 6 times with soap and water for an average of 15–20 seconds for each wash, the skin preparation maintains a protective barrier on the skin, wherein a protective barrier is one that is water-proof and prevents moisture from escaping from the skin and wherein at least about 75% of the skin preparation originally applied to the skin remains on the skin after each washing.

These and other features, aspects, and advantages of the present invention will become better understood with reference to the following description and appended claims.

DESCRIPTION

The present invention is directed to multipurpose skin preparations or compositions in the form of oil-in-water emulsions, which, when blended in accordance with the teaching of the present invention, provide excellent water-proof, respirable, and protective barriers on the skin, provide superior tactile properties, and effectively deliver and maintain moisturizing and therapeutic agents on the skin. It is believed that the skin preparations of the present invention also effectively deliver and maintain moisturizing and select therapeutic agents, biological agents, pharmaceutical agents, and the like, which are useful for the treatment of pathologies of the skin. The preparations of the present invention may be applied to the skin, i.e., the arms, the legs, the entire body, where conditioning or treatment is desired.

The skin preparations or compositions of the present invention preferably comprise oil-in-water emulsions, and in particular, oil-in-water emulsions containing silicones. Emulsions are generally formed from at least two liquid phases which are immiscible so that at least one of the phases is dispersed in fine form throughout the other phase(s). The components comprising each of the phases are discussed in detail below.

The Oil Phase

The oil phase, which for purposes of this application can also be referred to more specifically as the silicone phase, generally comprises a siloxane polymer, a cyclic silicone, at least one emulsifier, at least one anti-oxidant and at least one emollient. In a second version of the present invention, the silicone phase includes at least one copolymer formed from an isocyanate monomer and a polyol.

According to the teaching of the present invention, the oil phase is in an amount of from about 5% to about 25% by weight of the total weight of the skin preparation. Preferably, the oil phase is in an amount of from about 15% to about 20% by weight.

The oil phase includes a combination of silicone oils or silicone fluids. Preferably, the silicone oils or fluids comprise a siloxane polymer and a cyclic silicone. The siloxane polymer may include dimethicone, phenyltrimethicone, trimethylsiloxysilicate, or mixtures thereof. These siloxane polymers, discussed in detail below, have been assigned these names by the Cosmetic, Toiletry, and Fragrance Association (CTFA). However, other suitable siloxane polymers may also be used. In a first version of the present invention, the preferred siloxane polymers are dimethicone, trimethylsiloxysilicate, or mixtures thereof. In a second version of the present invention, the preferred siloxane polymers are dimethicone, trimethylsiloxysilicate, phenyltrimethicone, or mixtures thereof The siloxane polymers aid in the protective, water-proof, barrier function of the skin preparation, and also aid in giving the skin preparation a smooth powder-like, non-greasy feel after the skin preparation is applied to the skin.

The amount of siloxane polymer present in the oil phase is at least 2% by weight. The amount of siloxane polymer present in the oil phase may be in the range of from about 2% to about 7% by weight.

Dimethicone is a commercially available admixture of volatile and/or non-volatile polydimethylsiloxane polymers. Dimethicone is commercially available with average kinematic viscosities ranging from 50 to 1,000 centistokes (cst) at 25° C. Optimally, the dimethicone has a viscosity of 350 cst. The polydimethylsiloxanes which may be used in the present invention include medium viscosity silicone fluids which are commercially available from DOW CORNING of Midland, Mich., under the name 200® series (i.e., DOW CORNING® 200 FLUID).

Trimethylsiloxysilicate is a siloxane polymer in the form of a resin and silicone fluid that may also be used in the present invention. Trimethylsiloxysilicate is commercially available from Wacker-Chemie of Burgausen, Germany.

Phenyltrimethicone is an admixture of linear polyphenyltrimethylsiloxanes. Phenyltrimethicone is commercially available with an average kinematic viscosity of about 22 centistokes (cst) at 25° C. Phenyltrimethicone is commercially available from DOW CORNING of Midland, Mich., under the name DOW CORNING® 556 FLUID.

The most preferred siloxane polymer used in the present invention is an admixture of dimethicone (silicone fluid) and trimethylsiloxysilicate (silicone resin) that is commercially available from DOW CORNING of Midland, Mich., under the name DOW CORNING® 593 FLUID. DOW CORNING® 593 FLUID is commercially available with an average kinematic viscosity of about 650 centistokes (cst) at 25° C.

The oil phase also includes a cyclic silicone. The preferred cyclic silicone comprises cyclomethicone. However, other suitable cyclic silicones may also be used. Cyclomethicone is an admixture of volatile cyclic methylsiloxane compounds commercially available from DOW CORNING of Midland, Mich., under the name DOW CORNING® 245 FLUID, DOW CORNING® 344 FLUID, and DOW CORNING® 345 FLUID. DOW CORNING® 245, DC FLUID 344 AND DC FLUID 345 are commercially available with an average kinematic viscosity of about 2.5 centistokes (cst) at 25° C.

The amount of cyclic silicone present in the oil phase is at least 1% by weight. The amount of cyclic silicone present in the oil phase may be in the range of from about 1% to about 6% by weight. It is believed that the cyclic silicone aids in providing a smooth, powder-like, non-greasy feel when the skin preparation is applied to the skin, aids in the spreadability of the skin preparation, and aids in the delivery of the other silicones and other therapeutic components to the skin.

It is believed that the weight ratio of the siloxane polymer to the cyclic silicone in the oil phase is important to provide an optimum cross-linked, respirable protective barrier when the skin preparation is applied to the skin. The ratio of the weight of siloxane polymer to the weight of cyclic silicone in the oil phase of the present invention is at least 2:1. The ratio of the weight of siloxane polymer to the weight of cyclic silicone in the oil phase may be in the range of from about 2:1 to about 7:1. Preferably, the ratio of the weight of siloxane polymer to the weight of cyclic silicone is in the range of from about 3:1 to about 6:1. It is further believed that the specific combination and weight ratios of silicones create a protective barrier on the skin, as well as maintain and retain the protective barrier on the skin for a longer period of time and after multiple washings as compared to known preparations. An optimum protective barrier is one that substantially maintains a water-proof barrier, that allows the skin to respire, substantially prevents moisture from escaping from the skin, substantially protects the skin from irritants, and substantially delivers and maintains the therapeutic components on the skin, even after repeated washings of the skin with soap and water. Moreover, for purposes of this application, an optimum protective barrier is believed to be one that maintains at least 75% of the skin preparation originally applied to the skin on the skin even after multiple washings with soap and water at an average length of 15–20 seconds for each washing. It has been found that when the skin preparation is applied to the skin, a water-proof, protective coating or barrier is quickly formed. It is believed that with a first version of the present invention, that at least 75% of the skin preparation originally applied to the skin remains on the skin for an average of up to 3–4, or more, washings of the skin, where each washing is made with soap and water for an average of 15–20 seconds long. It is believed that with a second version of the present invention, that approximately 75% of the skin preparation originally applied to the skin remains on the skin for an average of up to 5–6, or more, washings of the skin, where each washing is made with soap and water for an average of 15–20 seconds long. Thus, the necessity for reapplications of the skin preparations of the present invention is decreased.

In a second version of the present invention, the oil phase includes a copolymer formed from an isocyanate monomer and a polyol. Preferably the copolymer is poly[oxy(methyl-1,2-ethandiyl)],α-hydro-ω-hydroxy polymer with 1,1'methylene-bis-[4,isocyanatocyclohexane] (CAS No. 9042-82-4), which has been assigned the name PPG-12/SMDI copolymer by the CTFA. PPG-12/SMDI copolymer is a copolymer of saturated methylene diphenyldiisocyanate and PPG-12 monomers, and is in the form of a thick liquid. PPG-12/SMDI is commercially available with an average kinematic viscosity of about 2500–4500 centipoise(cps) at 25° C. PPG-12/SMDI copolymer is commercially available from the company PENEDERM INC. of Foster City, Calif., under the name polyolprepolymer-2. However, other suitable copolymers may also be used in the present invention. The copolymer is present in an amount of at least 0.8% by weight of the total preparation. The copolymer may be present in an amount in the range of from about 0.8% to about 6% by weight.

It is believed that the use of the PPG12/SMDI copolymer aids in the water repellency and protective barrier function of the skin preparation, aids in anti-irritation, and aids in the delivery to the skin of the therapeutic components in the skin preparation.

The oil phase further comprises at least one emulsifier, which aids in stabilizing the emulsion. Preferably, a combination of emulsifiers is used. The emulsifier is present in an amount of at least 1.5% by weight of the total preparation. The emulsifier may be present in an amount in the range of from about 1.5% to about 10% by weight, and preferably from about 4% to about 6% by weight. Emulsifiers used in the present invention may include cetearyl alcohol, glyceryl stearate SE (self emulsifying), ceteareth-20, DEA (diethanolamine) cetyl phosphate, or mixtures thereof. However, other suitable emulsifiers in an effective amount may also be used. In a first version of the skin preparation, the preferred combination of emulsifiers includes cetearyl alcohol, glyceryl stearate SE, DEA cetyl phosphate, and ceteareth-20. In a second version of the skin preparation, the preferred combination of emulsifiers includes cetearyl alcohol, glyceryl stearate SE, and ceteareth-20. Cetearyl alcohol is a blend of high quality cetyl and stearyl alcohols and is commercially available from LIPO CHEMICALS INC. of Paterson, N.J. under the trade name LIPOCOL SC. Glyceryl stearate SE (CAS NO. 31566-31-1) consists of esters of glycerine and stearic acid and is commercially available from LIPO CHEMICALS INC. of paterson, N.J., under the trade name LIPO GMS 470. Ceteareth-20, a polyethylene glycol ether of cetearyl alcohol with 20 moles of ethylene oxide, is commercially available from HENKEL CORPORATION, EVERY GROUP of Ambler, Pa., under the trade name EUMULGIN B-2 (appearing as waxy flakes).

The oil phase further comprises at least one antioxidant which prevents or minimizes oxidation of the skin preparation from occurring and which counteracts free radical activity. Free radicals damage the skin by causing the deterioration of the skin's support structures, and by decreasing its elasticity and resilience, thus resulting in visible signs of aging. A combination of antioxidants may also be used. The antioxidant is present in an amount of at least 0.1% by weight of the total preparation. The antioxidant may be present in an amount in the range of from about 0.1% to about 10% by weight, preferably from about 1% to about 3% by weight. Preferably, the antioxidant used is dl-alpha tocopheryl acetate (Vitamin E) or tocopherol. However, other antioxidants commonly known and used may be used in amounts necessary to perform their respective functions. dL-alpha tocopheryl acetate is commercially available as a clear, yellow viscous oil from ROCHE VITAMINS, INC. of Parsippany, N.J.

The silicone phase further comprises at least one emollient. A combination of emollients may also be used. The emollient aids in spreadability and providing a smooth, powder-like, non-greasy feel when the skin preparation is applied to the skin. In addition, the emollient acts as a moisturizer to soothe and soften the skin and also aids in the barrier function of the skin preparation. The emollient is present in an amount of at least 2% by weight of the total skin preparation. The emollient may be present in an amount in the range of from about 2% to about 10% by weight, and preferably from about 4% to about 8% by weight. The emollient may include isopropyl palmitate, isopropyl myristate, octyl isononanoate, or mixtures thereof. However, other suitable emollients in an effective amount may also be used, such as lightweight esters including vegetable oils, safflower oil, or canola oil. In general, lightweight esters for purposes of this application include esters having an average kinematic viscosity of less than 10 centistokes (cst) at 25° C. In a first version of the skin preparation of the present invention, the preferred emollient used is isopropyl palmitate, isopropyl myristate, or a mixture thereof In a second version of the skin preparation of the present invention, the preferred emollient used is octyl isononanoate. Isopropyl myristate (isopropyl tetradecanoate, CAS NO. 110-27-0) is commercially available from ALDRICH CHEMICAL COMPANY of Milwaukee, Wis. Isopropyl palmitate (isopropyl hexadecanoate, CAS NO. 142-91-6) is commercially available from ALDRICH CHEMICAL COMPANY of Milwaukee, Wis. Octyl isononanoate (2-ethylhexyl alcohol and a branched chain nonanoic acid, CAS NO. 71566-49-9) is commercially available from STEPAN of Maywood, N.J.

Preservatives may also be incorporated into the oil phase in amounts effective to protect against the growth of potentially harmful microorganisms. In particular, in a second version of the present invention, the preservative propyl paraben may be present in at least 0.01% by weight of the total skin preparation. Propyl paraben may be present in an amount in the range of from about 0.01% to about 1% by weight, preferably about 0.05% by weight. Propyl paraben (propyl 4-hydroxybenzoate, CAS NO. 94-13-30) is commercially available from the ALDRICH CHEMICAL COMPANY of Milwaukee, Wis. Other suitable preservatives in an effective amount may also be used.

Other adjunct ingredients may also be added to the oil phase in their generally accepted manner in amounts effective for their intended purpose. Such adjunct ingredients may include anti-irritants, anti-bacterial agents, anti-fungals, and other therapeutically active ingredients, each in effective amounts to accomplish their respective functions. In the preferred embodiments, oat flour (Latin name: Avena Sativa, Tech-0-11070) may be present in an amount in the range of from about 0.1% to about 6.0% by weight of the total skin preparation, and preferably in an amount of about 0.5% by weight. Oat flour is commercially available from BEACON CMP CORPORATION of Kenilworth, N.J. Oat flour is believed to aid in anti-irritation, in spreadability of the skin preparation, and in providing a smooth feel on the skin.

In addition, in the preferred embodiments, tea tree oil, which is believed to aid as an antibacterial, antiseptic, fragrance component, and soothing component, may be present in an amount in the range of from about 0.001% to about 4.0% by weight of the total skin preparation, and preferably in an amount of about 0.02% by weight. Tea tree oil (Latin name: *Melaleuca alternifolia,* CAS NO. 68647-73-4) is commercially available from SIGMA CHEMICAL COMPANY of St. Louis, Mo.

The Aqueous Phase

The water phase, also referred to as the aqueous phase, is preferably in an amount in the range of from about 60% to about 90% by weight of the total weight of the skin preparation. The aqueous phase generally comprises water, at least one humectant, at least one rheology modifying agent, and at least one thickening agent.

Preferably, the water used in the present invention is deionized water. The amount of the water used in the skin preparations of the present invention is relative to the total amount of other components used such that the total weight of the skin preparation is equal to 100% by weight.

The aqueous phase further comprises a t least one humectant. Preferably, a combination of humectants is used in the present invention. Humectants are moisturizers, and are used to increase the moisture content of the skin and draw moisture from the air into the skin. The humectant(s) in the present invention is/are present in an amount of at least 0.1% by weight of the total skin preparation. The humectant(s) may be present in an amount in the range of from about 0.1% to about 10% by weight, and preferably in an amount of from about 3% to about 7% by weight. The identity and properties of specific humectants are generally known in the art and are set forth in U.S. Pat. No. 5,162,378, hereby incorporated by reference. The humectants used in the present invention may include propylene glycol, glycerin, hyaluronic acid, liquid panthenol (Vitamin B5), sorbitol, or mixtures thereof. However, other suitable humectants may also be used. Preferably, in a first version of the present invention, the humectants include glycerin, propylene glycol, liquid panthenol, hyaluronic acid and sorbitol. Preferably, in a second version of the present invention, the humectants include glycerin, liquid panthenol and hyaluronic acid.

The most preferred humectant is hyaluronic acid. The use of hyaluronic acid results in the need for much lower levels of emollients and lubricants in the formulations, thereby providing an essentially greaseless product. In addition, due to the ability of hyaluronic acid to retain water, it is not necessary that the product be applied to a smooth surface but rather when applied to a rough skin surface, it is made smooth. Hyaluronic acid is a polysaccharide, or more specifically a glycosaminoglycan. Hyaluronic acid is a high molecular weight polysaccharide with an unbranched backbone composed of alternating beta (1,4)-glucuronic acid and beta-(1,3)-N-acetylglucosamine linkages. The key property of hyaluronic acid which makes it an ideal ingredient is its ability to bind and hold more water than any other natural or synthetic polymer. This permits its use at very low levels, yet ensures its effectiveness as a delivery agent. The function of hyaluronic acid in the skin preparation of the present invention is as an aid both in moisturization and water retention. Hyaluronic acid is commercially available from TRI-K INDUSTRIES, INC. of Northvale, N.J.

Other humectants which may be used in the present invention include propylene glycol (1,2-propanediol, CAS NO. 4254-15-3) which is commercially available from ALDRICH CHEMICAL COMPANY of Milwaukee, Wis., and glycerin (glycerol, CAS NO. 56-81-5) which is commercially available from SIGMA CHEMICAL COMPANY of St. Louis, Mo. In addition, liquid panthenol is commercially available as liquid dl-panthenol (50% by weight in aqueous solution) from ROCHE VITAMINS, INC. of Parsippany, N.J. In addition, sorbitol (CAS NO. 50-70-4) is commercially available as 70% (by weight) solution in water from ALDRICH CHEMICAL COMPANY of Milwaukee, Wis.

The aqueous phase also comprises at least one rheology modifier. A combination of rheology modifiers may also be used. The rheology modifier aids in the flow and viscosity of the skin preparations. The rheology modifier is present in an amount of at least 0.1% by weight. The rheology modifier may be present in an amount in the range of from about 0.1% to about 2.0% by weight, and preferably in an amount of from about 0.2% to 1% by weight. In general, the rheology agent is a powder which is insoluble but dispersible in water. In the preferred embodiments, the rheology modifier used is magnesium aluminum silicate. However, other suitable rheology modifying agents may also be used, such as other suitable inorganic salt complexes. Magnesium aluminum silicate is commercially available under the trade name VEEGUM ULTRA from R.T. VANDERBILT COMPANY, INC. of Norwalk, Conn.

The aqueous phase further comprises at least one thickener. Preferably, a combination of thickeners is used. The thickener is used to aid in holding the emulsion together and also aids in providing a smooth feel. The thickener is present in an amount of at least 0.1% by weight of the total skin preparation. The thickener is present in an amount in the range of from about 0.1% to about 3% by weight, and preferably in an amount of from about 0.7% to about 2% by weight. In the preferred embodiments, the thickeners used include hydroxyethylcellulose, xanthan gum, or mixtures thereof. However, other suitable thickeners may also be used. Hydroxyethylcellulose, a hydroxyethyl ether of cellulose (CAS NO. 9004-52-0) is commercially available under the trade name NATROSOL 250 HHR from AQUALON of Parlin, N.J. Xanthan gum (CAS NO. 11138-66-2) is commercially available from the ALDRICH CHEMICAL COMPANY of Milwaukee, Wis.

Other adjunct ingredients may also be added to the aqueous phase in accepted manners known to practitioners of ordinary skill in the art. Such adjunct ingredients may include anti-irritants, anti-bacterial agents, anti-fungals, electrolytes, and other therapeutically active ingredients, each in amounts effective to accomplish their respective function.

In the preferred embodiments, allantoin may be added to the aqueous phase to aid in anti-irritation and provide a soothing feel. In addition, allantoin aids in reducing inflammation. The allantoin may be present in an amount in the range of from about 0.05% to about 2.0% by weight of the total skin preparation, and preferably from about 0.01% to about 1%. Allantoin (5-ureidohydantoin, CAS NO. 97-59-6) is commercially available from ALDRICH CHEMICAL COMPANY of Milwaukee, Wis.

Preservatives may also be added to the aqueous phase in amounts effective to protect against the growth of potentially harmful microorganisms. Preferably, a combination of preservatives may be used. Preferred preservatives that may be used in the aqueous phase include phenoxyethanol, methylparaben, potassium sorbate, or mixtures thereof. However, other suitable preservatives may also be used. The preservative or combination of preservatives may be present in an amount of from about 0.1% to about 5% by weight of the total skin preparation, and preferably, in an amount of from about 1% to about 3% by weight. Phenoxyethanol (2-phenoxyethanol, CAS No. 122-99-6) is commercially available from the ALDRICH CHEMICAL COMPANY of Milwaukee, Wis. Methylparaben (methyl 4-hydroxybenzoate, CAS NO.99-76-3) is commercially available from ALDRICH CHEMICAL COMPANY of Milwaukee, Wis. Potassium sorbate (an organic salt, CAS NO. 590-00-1) is commercially available from EASTMAN CHEMICAL COMPANY of Kingsport, Tenn.

Post Combination Components

Additional components may be further added to the emulsion after the oil phase and the aqueous phase have been combined or mixed together. As will be more fully described in detail below, the skin preparations of the present invention are generally made by first making the oil phase and the aqueous phase in separate vessels and then combining the phases together with mixing. For purposes of this application, components added to the emulsion after the oil and aqueous phases are sufficiently combined are referred to as "post combination components" Such post combination components may include preservatives, botanical extracts, fragrances, sun screens, pharmaceuticals, steroids, and other desirable components.

For example, botanical extracts may be added in effective amounts to accomplish their respective functions after the oil phase and aqueous phase are combined. In the preferred embodiments, botanical extracts are added to the cooled combined phases just prior to the end of the mixing. Botanical extracts used in the present invention may include Japanese green tea extract, chamomile extract, balm mint extract, lavender oil, witch hazel extract, or mixtures thereof. Other suitable botanical extracts or products in an effective amount may also be used. In a first version of the present invention, the preferred botanical extracts used include Japanese green tea extract, chamomile extract, balm mint extract, lavender oil, and witch hazel extract. In a second version of the present invention, the preferred botanical extracts used include Japanese green tea extract, chamomile extract, balm mint extract, and lavender oil. The Japanese green tea extract is commercially available as Actiphyte of Japanese Green Tea Concentrate (appearing as a light to yellow liquid) from the company ACTIVE ORGANICS of Dallas, Tex. The chamomile extract is assigned the name Matricaria Extract by the CTFA/INCI (Cosmetic, Toiletry, and Fragrance Association/International Nomenclature of Cosmetic Ingredients) and is commercially available as ACTIPHYTE OF CHAMOMILE (appearing as a light to medium amber liquid) from the company ACTIVE ORGANICS of Dallas, Tex. The balm mint extract is commercially available (appearing as a light to medium amber liquid) from ACTIVE ORGANICS of Dallas, Tex. The lavendar oil is commercially available from ACTIVE ORGANICS of Dallas, Tex. The witch hazel extract is commercially available from ACTIVE ORGANICS of Dallas, Tex.

Preservatives may also be added after the oil phase and the aqueous phase have been combined, and may be added in amounts effective to protect against growth of potentially harmful microorganisms. In a first version of the present invention, the preservative diazolidinyl urea may be added after the oil and aqueous phases are combined. However, other suitable preservatives may also be used. Diazolidinyl urea (CAS NO. 78491-02-8) is commercially available from SIGMA CHEMICAL COMPANY of St. Louis, Mo.

The emulsions of the present invention are generally made by first making the oil phase and the aqueous phase in separate vessels and then combining the oil and aqueous phases, with stirring, at a temperature of about 70° C. to about 80° C. Preferably, the oil phase and the aqueous phase are made simultaneously and mixed in separate vessels. The size and type of mixing vessel used depends on the amount of preparation prepared. For example, for mixing large batches, stainless steel tanks or other containers known in the art may be used.

The oil phase is made by mixing the oil phase components together with constant stirring in a mixing vessel separate from the mixing vessel containing the aqueous phase components. The oil phase components are mixed sufficient time and heated to a temperature of from about 70° C. to about 80° C. The amount of time that the oil phase components are mixed together depends on the size of the mixing vessel used, and thus adequate mixing time may range from minutes to hours.

The aqueous phase is made by first obtaining any solid components, such as the thickener(s), rheology modifier(s), and the like, and dry-blending them together and then slowly sifting them into the center of a mixing vortex of water. The water is slowly heated to a temperature of from about 70° C. to about 80° C. When the temperature approaches 70° C., the desired humectants and optional preservatives are then added. The amount of time that the aqueous phase ingredients are mixed together depends on the size of the mixing vessel used, and thus adequate mixing time may range from minutes to hours.

The oil phase (at 70° C.–80° C.) is then mixed together with the water phase (at 70° C. to 80° C.) with constant agitation. Mixing of the two phases may occur in the same vessel or tank that the oil phase or aqueous phase is originally mixed in. The resultant mixture is cooled at ambient temperature (approximately 25° C.) in a cooled water bath, a jacketed tank having cool water running through it, or some other type of known cooling vessel, until the mixture reaches a temperature of 40° C. At the temperature of 40° C., mixing is slowed slightly and any desired preservative(s), botanical material(s), or other components may be blended into homogeneity with the continued slowed mixing. The mixture is then cooled to below 35° C. The mixture may then be stored in a sealed container and then packaged.

The following examples will more fully illustrate select versions of the invention. These examples are meant to illustrate, but not to limit, the subject invention. All parts, percentages and proportions referred to here and in the appended claims are by weight (total composition) unless otherwise indicated.

EXAMPLE 1

The method of making a first version of the present invention using the below listed components in Table 1 is now described. All components are listed in a weight percent of the total weight of the skin preparation or composition.

TABLE I

| Component | Weight % of total |
| --- | --- |
| OIL PHASE | |
| Dimethicone - 350 cst | 1.50 |
| Cyclomethicone | 1.60 |
| Dow Corning ® 593 | 0.95 |
| Cetearyl alcohol | 1.00 |
| Ceteareth-20 (Eumulgin B-2) | 0.60 |
| Glyceryl stearate, S.E. (Lipo GMS 470) | 2.65 |
| DEA cetyl phosphate (Amphisol) | 0.50 |
| Isopropyl palmitate | 4.00 |
| Isopropyl myristate | 2.50 |
| Tea tree oil | 0.02 |
| Oat flour (Tech-0-11070) | 0.35 |
| AQUEOUS PHASE | |
| Deonized water | 72.29 |
| Magnesium Aluminum Silicate (Veegum ultra) | 0.40 |
| Hydroxyethylcellulose (Natrosol 250 hhr) | 0.45 |
| Xanthan gum | 0.25 |
| Glycerin | 3.00 |
| Propylene glycol | 2.00 |
| 50% liquid panthenol | 1.00 |
| Hyaluronic acid | 0.10 |

TABLE I-continued

| Component | Weight % of total |
| --- | --- |
| Sorbitol (70%) | 0.50 |
| Allantoin | 0.10 |
| Methylparaben | 0.25 |
| Potassium sorbate | 0.25 |
| Phenoxyethanol | 0.80 |
| POST COMBINATION COMPONENTS | |
| Chamomile extract | 1.00 |
| Balm mint extract | 0.50 |
| Japanese green tea concentrate | 1.00 |
| Lavender oil | 0.04 |
| Witch hazel extract | 0.20 |
| Diazolidinyl urea | 0.20 |

The oil phase components (Table I) are mixed together in a stainless steel tank and heated to a temperature of between about 75° C. and 80° C. for approximately 20 minutes with constant stirring in the form of a propeller-type mixer.

At the same time that the oil phase components are mixed together, the aqueous phase components (Table I) are mixed together. The required amount of deionized water is first measured into a separate stainless steel mixing tank and is mixed with a propeller-type mixer at about 25° C. In a separate vessel, the magnesium aluminum silicate, xanthan gum, hydroxyethylcellulose, and allantoin are dry blended and then slowly sifted into a vortex with the water, with, preferably high speed mixing. Mixing is continued for about 20 minutes until a homogenous dispersion is obtained. At that time, the remainder of the aqueous phase materials (as listed in Table I) are added and the heating process is begun. Heating is continued until the aqueous phase reaches a temperature of between 75° C. and 80° C. Once it reaches the desired temperature, the mixture is mixed with side sweep motion type mixing for about 15 minutes. Side sweep motion type mixing is known in the art and involves using a stainless steel tank having a central mixing area and where the blades of the mixer move from the center of the tank to the sides of the tank and scrape the inside of the tank to prevent the material being mixed from adhering to the inside of the tank. The total amount of time for mixing the aqueous phase is about 35 minutes.

When both the water phase and oil phase have reached temperatures of between 75° C. and 80° C., the oil phase is added to the water phase with constant mixing, such as side sweep mixing. The temperature of between about 75° C. and 80° C. is maintained for 15 minutes with stirring, then the batch is cooled to a temperature of about 40° C. The mixture is cooled with a jacketed tank that has cool water running through it. When the mixture reaches a temperature of about 40° C., the remaining ingredients are added, with mixing, and the resultant preparation is cooled, with mixing, until the batch reaches room temperature.

EXAMPLE 2

The method of making a second version of the present invention using the below listed components in Table II is now described. All components are listed in a weight percent of the total weight of the skin preparation or composition.

TABLE II

| Component | Weight % of total |
| --- | --- |
| OIL PHASE | |
| Dimethicone - 350 cst | 1.5 |
| Cyclomethicone | 1.8 |
| Dow Corning ® 593 | 2.0 |
| PPG-12/SMDI copolymer | 2.0 |
| Phenyltrimethicone | 2.0 |
| Cetearyl alcohol | 1.0 |
| Ceteareth-20 (Eumulgin B-2) | 1.0 |
| Glyceryl stearate, S.E. (Lipo GMS 470) | 3.0 |
| Octyl isononanoate | 6.0 |
| Tocopheryl acetate | 0.25 |
| Oat flour (Tech-0-11070) | 0.35 |
| Tea tree oil | 0.03 |
| Propylparaben | .05 |
| AQUEOUS PHASE | |
| Deonized water | 72.90 |
| Magnesium Aluminum Silicate (Veegum Ultra) | 0.40 |
| Hydroxyethylcellulose (Natrosol 250 HHR) | 0.45 |
| Xanthan gum | 0.25 |
| Glycerin | 3.00 |
| 50% liquid panthenol | 2.00 |
| Hyaluronic acid | 0.05 |
| Allantoin | 0.15 |
| Methylparaben | 0.20 |
| Potassium sorbate | 0.25 |
| Phenoxyethanol | 0.85 |
| POST COMBINATION COMPONENTS | |
| Chamomile extract | 1.00 |
| Balm mint extract | 0.80 |
| Japanese green tea concentrate | 1.00 |
| Lavender oil | 0.05 |
| Witch hazel extract | 0.20 |
| Diazolidinyl urea | 0.20 |

The oil phase components (Table II) are mixed together in a stainless steel tank and heated to a temperature of between about 75° C. and 80° C. for approximately 20 minutes with constant stirring in the form of a propeller-type mixer.

At the same time that the oil phase components are mixed together, the aqueous phase components (Table II) are mixed together. The required amount of deionized water is first measured into a separate stainless steel mixing tank and is mixed with a propeller-type mixer at about 25° C. In a separate vessel, the magnesium aluminum silicate, xanthan gum, hydroxyethylcellulose, and allantoin are dry blended and then slowly sifted into a vortex with the water, with, preferably high speed mixing. Mixing is continued for about 20 minutes until a homogenous dispersion is obtained. At that time, the remainder of the aqueous phase materials (as listed in Table II) are added and the heating process is begun. Heating is continued until the aqueous phase reaches a temperature of between 75° C. and 80° C. Once it reaches the desired temperature, the mixture is mixed with side sweep motion type mixing for about 15 minutes. Side sweep motion type mixing is known in the art and involves using a stainless steel tank having a central mixing area and where the blades of the mixer move from the center of the tank to the sides of the tank and scrape the inside of the tank to prevent the material being mixed from adhering to the inside of the tank. The total amount of time for mixing the aqueous phase is about 35 minutes.

When both the water phase and oil phase have reached temperatures of between 75° C. and 80° C., the oil phase is added to the water phase with constant mixing, such as side sweep mixing. The temperature of between about 75° C. and 80° C. is maintained for 15 minutes with stirring, then the batch is cooled to a temperature of about 40° C. The mixture is cooled with a jacketed tank that has cool water running through it. When the mixture reaches a temperature of about 40° C., the remaining ingredients are added, with mixing, and the resultant preparation is cooled, with mixing, until the batch reaches room temperature.

Although the present invention has been described in considerable detail with reference to certain preferred versions thereof, other versions are possible. Therefore, the scope of the appended claims should not be limited to the description of the preferred versions contained herein.

What is claimed is:

1. A skin preparation comprising,
   a) an oil phase including;
      (i) a siloxane polymer, selected from the group consisting of dimethicone, trimethylsiloxysilicate, and mixtures of dimethicone and trimethylsiloxysilicate, in an amount of at least about 2% by weight of the total skin preparation;
      (ii) a cyclic silicone in an amount of at least about 1% by weight of the total skin preparation; wherein the siloxane polymer and cyclic silicone are present in a ratio by weight in the range of from about 2:1 to about 7:1;
      (iii) one or more emulsifiers in an amount of at least about 1.5% by weight of the total skin preparation;
      (iv) one or more antioxidants in an amount of at least about 0.1% by weight of the total skin preparation; and
      (v) one or more emollients in an amount of at least about 2% by weight of the total skin preparation;
      (vi) one or more oil soluble therapeutic agents in an amount of at least 0.001% by weight of the total skin preparation; and
   b) an aqueous phase including;
      (i) one or more humectants in an amount of from at least about 0.1% to about 8% by weight of the total skin preparation;
      (ii) one or more rheology modifiers in an amount of at least about 0.1% by weight of the total skin preparation;
      (iii) one or more thickeners in an amount of at least about 0.1% by weight of the total skin preparation;
      (iv) one or more water soluble therapeutic agents in an amount of at least 0.1% by weight of the total skin preparation; and
      (v) water.

2. The skin preparation of claim 1, where the skin preparation contains a sufficient amount of siloxane polymer and a sufficient amount of cyclic silicone such that after the skin preparation is applied to the skin and a coating is formed on the skin, when the skin is washed 3 to 4 times with soap and water for a length of time from about 15 seconds to 20 seconds each washing, the skin preparation maintains a protective barrier and effectively delivers said oil soluble and water soluble therapeutic agents to the skin.

3. A skin preparation comprising:
   a) an oil phase including;
      (i) a siloxane polymer, selected from the group consisting of dimethicone, trimethylsiloxysilicate, phenyl trimethicone, and mixtures of dimethicone, trimethylsiloxysilicate, and phenyl trimethicone, in an amount of at least about 2% by weight of the total skin preparation;
      (ii) a cyclic silicone in an amount of at least about 1% by weight of the total skin preparation;
      (iii) polyolprepolymer-2 in an amount of at least about 0.8% by weight of the total skin preparation;

(iv) one or more emulsifiers in an amount of at least about 1.5% by weight of the total skin preparation;
(v) one or more antioxidants in an amount of at least about 0.1% by weight of the total skin preparation; and,
(vi) one or more emollients in an amount of at least about 2% by weight of the total skin preparation;
(vii) one or more oil soluble therapeutic agents in an amount of at least 0.001% by weight of the total skin preparation; and b) an aqueous phase including;
(i) one or more humectants in an amount of from at least about 0.1% to about 8% by weight of the total skin preparation;
(ii) one or more rheology modifiers in an amount of at least about 0.1% by weight of the total skin preparation;
(iii) one or more thickeners in an amount of at least about 0.1% by weight of the total skin preparation;
(iv) one or more water soluble therapeutic agents in an amount of at least 0.1% by weight of the total skin preparation; and
(v) water.

4. The skin preparation of claim 3, where the siloxane polymer and cyclic silicone are present in a ratio by weight in the range of from about 2:1 to about 7:1.

5. The skin preparation of claim 3, where the skin preparation contains a sufficient amount of polyolprepolymer-2 such that after the skin preparation is applied to the skin and a coating is formed on the skin, when the skin is washed up to 5 to 6 times with soap and water for a length of time from about 15 seconds to about 20 seconds for each washing, the skin preparation maintains a protective barrier and effectively delivers said oil soluble and water soluble therapeutic agents to the skin.

6. An oil-in-water emulsion skin preparation comprising,
a) an oil phase including;
(i) a siloxane polymer selected from the group consisting of dimethicone, trimethylsiloxysilicate, phenyl trimethicone, and mixtures of dimethicone, trimethylsiloxysilicate, and phenyl trimethicone, where the siloxane polymer is present in an amount of at least about 2% by weight of the total skin preparation;
(ii) a cyclic silicone comprising cyclomethicone where the cyclic silicone is present in an amount of at least about 1% by weight of the total skin preparation; wherein the siloxane polymer and cyclic silicone are present in a ratio by weight of from about 2:1 to about 7:1;
(iii) one or more emulsifiers selected from the group consisting of cetearyl alcohol, glyceryl stearate, ceteareth-20, diethanolamine cetyl phosphate, and mixtures of cetearyl alcohol, glyceryl stearate, ceteareth-20, diethanolamine and cetyl phosphate, where the one or more emulsifiers are present in an amount of at least about 1.5% by weight of the total skin preparation;
(iv) an antioxidant comprising tocopheryl acetate in an amount of at least about 0.1% by weight of the total skin preparation; and,
(v) one or more emollients selected from the group consisting of isopropyl myristate, isopropyl palmitate, octyl isononoate, and mixtures of isopropyl myristate, isopropyl palmitate and octyl isononoate where the one or more emollients are present in an amount of at least about 2% by weight of the total skin preparation; and b) an aqueous phase including;
(i) one or more humectants selected from the group consisting of glycerin, hyaluronic acid, panthenol, sorbitol, propylene glycol, and mixtures of glycerin, hyaluronic acid, panthenol, sorbitol, and propylene glycol, where the one or more humectants are present in an amount from at least 0.1% to about 8% by weight of the total skin preparation;
(ii) one or more rheology modifiers comprising magnesium aluminum silicate, where the one or more rheology modifiers are present in an amount of at least about 0.1% by weight of the total skin preparation;
(iii) one or more thickeners selected from the group consisting of hydroxyethylcellulose, xanthan gum, and mixtures of hydroxyethylcellulose, xanthan gum, where the one or more thickeners are present in an amount of at least about 0.1% by weight of the total skin preparation; and
(iv) water.

7. The skin preparation of claim 6, where the oil phase further includes optionally, polyolprepolymer-2 in an amount of at least about 0.8% by weight of the total skin preparation.

8. The skin preparation of claim 1 further including at least about 0.01% by weight of the total skin preparation of a preservative and at least 0.20% by weight of the total skin preparation of a botanical.

9. The skin preparation of claim 3 further including at least about 0.01% by weight of the total skin preparation of a preservative and at least 0.20% by weight of the total skin preparation of a botanical.

10. The skin preparation of claim 6 further including at least about 0.01% by weight of the total skin preparation of a preservative selected from the group consisting of propyl paraben, phenoxy ethanol, methylparaben, diazolidinyl urea and potassium sorbate; and at least 0.20% by weight of the total skin preparation of a botanical, selected from the group consisting of Japanese green tea extract, chamomile extract, balm mint extract, lavender oil, and witch hazel.

11. The skin preparation of claim 6 further including, in the oil phase, a first therapeutic agent, selected from the group consisting of oat flour, tea tree oil and a mixture of oat flour and tea tree oil, in an amount of at least 0.001% by weight of the total skin preparation; and, in the aqueous phase, allantoin in an amount of at least 0.1% by weight of the total skin preparation.

* * * * *